US008041084B2

(12) United States Patent
Fenrich et al.

(10) Patent No.: US 8,041,084 B2
(45) Date of Patent: Oct. 18, 2011

(54) SYSTEM AND METHOD FOR COLLECTING DNA AND FINGERPRINTS

(75) Inventors: Richard K. Fenrich, Blacksburg, VA (US); Jennifer E. Robertson, Blacksburg, VA (US); James David Rancourt, Blacksburg, VA (US)

(73) Assignee: Identification International, Inc., Blacksburg, VA (US)

(*) Notice: Subject to any disclaimer, the term of this patent is extended or adjusted under 35 U.S.C. 154(b) by 1336 days.

(21) Appl. No.: 11/638,436

(22) Filed: Dec. 14, 2006

(65) Prior Publication Data

US 2010/0284574 A1  Nov. 11, 2010

Related U.S. Application Data

(63) Continuation of application No. 10/420,918, filed on Apr. 23, 2003, now Pat. No. 7,308,123.

(60) Provisional application No. 60/374,488, filed on Apr. 23, 2002.

(51) Int. Cl.
*G06K 9/00* (2006.01)

(52) U.S. Cl. ........ 382/125; 382/126; 382/129; 382/140; 382/143

(58) Field of Classification Search .................. 382/124, 382/125, 127, 128, 129, 140, 143; 435/6
See application file for complete search history.

(56) References Cited

U.S. PATENT DOCUMENTS

| | | | |
|---|---|---|---|
| 3,982,836 A | 9/1976 | Green et al. | |
| 4,120,585 A | 10/1978 | DePalma et al. | |
| 4,340,300 A | 7/1982 | Ruell | |
| 4,707,235 A | 11/1987 | Englert et al. | ............. 204/182.8 |
| 4,823,007 A | 4/1989 | Hanson | ....................... 250/327.2 |
| 5,073,495 A | 12/1991 | Anderson | ...................... 435/284 |
| 5,671,090 A | 9/1997 | Pernick et al. | |
| 5,751,835 A | 5/1998 | Topping et al. | |
| 5,764,347 A | 6/1998 | Podmaniczky et al. | |
| 6,069,969 A * | 5/2000 | Keagy et al. | .................. 382/124 |
| 6,140,936 A * | 10/2000 | Armstrong | ................... 340/5.74 |
| 6,150,665 A | 11/2000 | Suga | |
| 6,162,485 A | 12/2000 | Chang | |
| 6,168,922 B1 | 1/2001 | Harvey et al. | |
| 6,185,319 B1 | 2/2001 | Fujiwara | |

(Continued)

FOREIGN PATENT DOCUMENTS

WO WO 97/18009 5/1997

OTHER PUBLICATIONS

Murphy, Stephanie, "Print Makers: Company's fingerprint technology at use in Afghanistan—and PBIA", Palm Beach Daily News, p. D1 and D6 (Nov. 24, 2002).

(Continued)

*Primary Examiner* — Samir Ahmed
*Assistant Examiner* — Ali Bayat
(74) *Attorney, Agent, or Firm* — Pillsbury Winthrop Shaw Pittman LLP

(57) ABSTRACT

A system and method is provided that simultaneously or consecutively collects DNA samples and ridge and valley signatures from the same subject during the same collection window that adds value to forensic data collection processes. The collection of the DNA samples and ridge and valley signatures occur during the same collection window to assured the DNA sample and ridge and valley signatures identify the same individual.

8 Claims, 8 Drawing Sheets

U.S. PATENT DOCUMENTS

| | | | |
|---|---|---|---|
| 6,219,439 | B1 | 4/2001 | Burger |
| 6,229,906 | B1 | 5/2001 | Pu et al. |
| 6,355,439 | B1 * | 3/2002 | Chung et al. ............... 435/6 |
| 6,372,484 | B1 * | 4/2002 | Ronchi et al. ............ 435/287.2 |
| 6,917,902 | B2 | 7/2005 | Alexander |
| 7,027,932 | B2 | 4/2006 | Okawa ............... 702/19 |
| 7,308,123 | B2 * | 12/2007 | Fenrich et al. ............ 382/125 |
| 2001/0000749 | A1 * | 5/2001 | Zinn et al. ............... 435/6 |
| 2002/0031245 | A1 * | 3/2002 | Rozenberg et al. ......... 382/125 |
| 2002/0037094 | A1 | 3/2002 | Salva Calcagno |
| 2003/0056113 | A1 | 3/2003 | Korosec |
| 2003/0085274 | A1 * | 5/2003 | Leaton et al. ............ 235/380 |
| 2003/0113906 | A1 * | 6/2003 | Sangha et al. ............ 435/287.2 |
| 2003/0149661 | A1 | 8/2003 | Mitchell et al. |
| 2004/0014080 | A1 * | 1/2004 | Tanga et al. ............... 435/6 |
| 2005/0019898 | A1 | 1/2005 | Adey et al. |
| 2006/0170906 | A1 | 8/2006 | Arnold et al. |

OTHER PUBLICATIONS www.crossmatch.com/products_singlescan_v50.html (at least as early as Apr. 11, 2003).

www.crossmatch.com/products_singlescan_v30.html (at least as early as Apr. 11, 2003).

www.crossmatch.com/products_singlescan_vE.html#system (at least as early as Apr. 11, 2003).

Cross Match Technologies, Inc., "ID 1000 10 Print Live Scan System" (at least as early as Apr. 11, 2003).

www.crossmatch.com/products_overview_.html (at least as early as Apr. 11, 2003).

www.crossmatch.com/products_livescan_id10.html (at least as early as Apr. 11, 2003).

Cross Match Technologies, Inc., "Cross Country Bank Using Cross Match Technologies Biometric Fingerprinting Solution to Speed Up Background Checks" (Nov. 5, 2002).

Cross Match Technologies, Inc., "Union Bank of California Selects Live Scan Fingerprint Systems From Cross Match Technologies to Fight Fraud" (Nov. 18, 2002).

Cross Match Technologies, Inc., "Cross Match ® Providing Equipment to Interprint's ID Card Solution in Sao Paulo, Brazil" Dec. 11, 2002.

Cross Match Technologies, Inc., "Cross Match Technologies Names First-Ever COO to Manage Substantial Growth of the Company" (Jan. 9, 2003).

Cross Match Technologies, Inc., "First Tennessee National Corporation Selects Live Scan Fingerprint Solution From Cross Match Technologies for Employee Background Checks" (Feb. 25, 2003).

www.crossmatch.com/index2.html (at least as early as Apr. 11, 2003).

Sun® Microsystems, "Sun Microsystems Teams Up with Biometrics Technology Leaders to Deliver One-of-a-Kind, High-Security, Biometric Access Solution" (Mar. 4, 2003).

www.crossmatch.com/products_access.html (at least as early as Apr. 11, 2003).

www.crossmatch.com/products_mobilescan.html (at least as early as Apr. 11, 2003).

www.crossmatch.com/products_mv5bcs.html#specs2 (at least as early as Apr. 11, 2003).

Cross Match Technologies, Inc., "MV5: Mobile Fingerprint Scanner" (at least as early as Apr. 11, 2003).

Cross Match Technologies, Inc., Verifier™ 300: Single Finger Scanner with USB or Video Interface (at least as early as Apr. 11, 2003).

www.secugen.com (at least as early as Apr. 11, 2003).

Motorola Mediacenter—Press Release "Motorola to Provide LiveScan Technology to Southwest Alabama Integrated Criminal Justice System" (Dec. 20, 2002) www.motorola.com/mediacenter/news/detail/0, 1958,2238_182.

www.identix.com/products/pro_livescan.html (at least as early as Apr. 11, 2003).

www.hbs-jena.com/Products/body_products.html (at least as early as Apr. 11, 2003).

* cited by examiner

SYSTEM AND METHOD FOR COLLECTING DNA AND FINGERPRINTS This application is a continuation of U.S. application Ser. No. 10/420,918, filed Apr. 23, 2003, now U.S. Pat. No. 7,308,123, which claims priority from U.S. Provisional Patent Application No. 60/374,488 filed on Apr. 23, 2002, each of which are incorporated herein by reference in its their entirety.

BACKGROUND OF THE INVENTION

1. Field of the Invention

The present invention provides a system and method for the collection of a DNA sample(s) and ridge and valley signature(s) from a subject during a continuous time slot, hereinafter called a collection window. More particularly, the present invention provides for both simultaneous and combined collection of samples of DNA and ridge and valley signatures from a subject during a single collection window. Most particularly, the present invention provides for both simultaneous and combined collection in a single physical location of forensic quality samples of DNA and ridge and valley signatures from a subject during a single collection window of no more than about 45 or no more than about 30 minutes duration or no more than about 15 minutes duration.

2. Description of the Related Art

Humans have ridges and valleys on their hands and feet. A ridge and valley signature is the pattern formed by the ridges and valleys within at least one of the areas within the hands and feet. Ridge and valley impressions from a subject's fingers are commonly known as fingerprints. Animals also commonly have unique patterns on their footpads. In dogs and cats, for example, these patterns are called paw prints.

Many entities collect demographic and ridge and valley signature data to verify a subject's identity or to preserve a subject's uniquely identifying ridge and valley signatures for later use. Ridge and valley data are typically collected using paper and ink or optical imaging systems. Biometrics is the science of using digital technology to identify individuals based on that individual's unique physical and biological qualities, e.g., fingerprints, iris scans, and DNA. These biological qualities can be captured at different levels with the most useful and accurate being forensic quality. For example, the U.S. Federal Bureau of Investigation maintains standards for forensic quality ridge and valley signature capture and transmission. The standards are set forth in the following documents, the entire contents of which are incorporated herein by reference:

Data Format for the Interchange of Fingerprint Information, ANSI/NIST-CSL 1-1993.

Electronic Fingerprint Transmission Specification, Federal Bureau of Investigation, March 1998, CJIS-RS-0010 (V6R2).

When ridge and valley signatures are captured according to these standards, the signatures are said to be of forensic quality. Among other attributes, forensic quality signatures must digitally represent the ridge and valley patterns of an individual as an image with at least 500 dots per inch resolution.

Another biometric tool that has been increasingly used in the law enforcement field is DNA association with an individual. It should be understood that in the text of this patent that "DNA sample" and "DNA bearing sample" both mean a biological sample that contains DNA which can be analyzed with scientific methods. The Federal Bureau of Investigation maintains a DNA database, called the Combined DNA Index System, or CODIS, through which Federal, State, and Local law enforcement agencies may request forensic DNA matching. The forensic quality of CODIS and any State or Local DNA database is maintained by using recognized DNA sampling guidelines. These guidelines are:

1. The system monitor collecting a DNA sample must wear clean, dry rubber gloves and change them between collecting samples.
2. Any instruments used by a system monitor for the collection of a DNA sample (e.g., scissors, swabs, etc) must either be disposed of or thoroughly cleaned and dried between collecting samples.
3. The system monitor collecting a DNA sample must avoid touching the area where the DNA is located.
4. The system monitor collecting a DNA sample must not sneeze, cough, talk, or otherwise release saliva over the sample.
5. The system monitor collecting a DNA sample must not touch his/her face or other body parts while collecting the sample.
6. The system monitor collecting a DNA sample must ensure than no hairs, eyelashes, or other such personal substances of the system monitor touch the DNA sample.
7. The collected DNA sample must be completely air-dried before packaging and, preferably, the drying environment should be sterile to prevent environmental contamination.
8. The collected and air-dried DNA sample should be placed into a new, clean, dry, paper bag for transportation and not in a plastic bag, since plastic bags can retain moisture that can degrade the forensic quality of the DNA sample.
9. Externally applied tape should be used to securely close a bag containing a DNA sample as staples can physically harm the DNA sample, or chemically contaminate it.
10. A DNA sample must be stored in a cool, dry location, out of direct sunlight because sunlight, heat, and moisture can damage the DNA sample.
11. All DNA samples must be packaged independently of one another to avoid cross-contamination.
12. The DNA sample collection medium, such as adhesive paper or tape, must never be exposed to the environment until the DNA sample is to be taken, and should be kept in a sterile package until needed, in order to prevent environmental contamination.

The following documents provide further background information concerning DNA collection standards and the entire contents of each are incorporated herein by reference.

What Every Law Enforcement Officer Should Know About DNA Evidence. National Institute of Justice, Brochure #BC000614, NIJ, September 1999. http://www.ncjrs.org/pdffilesl/nij/bc000614.pdf Collection and Preservation of Evidence. Schiro, George, La. State Police Crime Laboratory. http://www.crime-scene-investigator.net/evidenc3.html Collection Of Deoxyribonucleic Acid (DNA) Reference Specimens To Aid In Remains Identification, Commandant of the Marine Corps, Marine Corps Order #MCO 1771.1A, Jun. 15, 1999. http://www.usmc.mil/directiv.nsf/df51342d91236d2685256517004eb0 26/883ca1c315d11fe9852568500061751a?OpenDocument Evidence Handling Guide, L.A. Department of Public Safety and Corrections, Office of State Police, Crime Laboratory.

Early patents directed to capture and enhancement of images of fingerprints did not yield forensic quality prints and/or did not capture a subject's DNA. For example, U.S. Pat. Nos. 3,982,836, 4,120,585, and 4,340,300 all issued well prior to the FBI's definition of forensic quality prints therefore these systems had not been designed with these exacting standards in mind. Likewise, such fingerprinting patents make no provision for collection of DNA samples. U.S. Pat. No. 3,982,836 to Green et al., the entire contents of which are incorporated herein by reference, teaches a transparent pressure-sensitive gel for capturing a pattern of a finger being pressed thereon, through which gel a beam of polarized collimated light is passed and the modified light beam emitted by the gel being projected through a polarization analyzer to produce an enhanced image of the fingerprint that is input to an image comparator.

U.S. Pat. No. 4,120,585 to De Palma et al., the entire contents of which are incorporated herein by reference, teaches a pliable optical prism that deforms to partially capture a mirrored topographic configuration of the surface of a finger pressed thereon, for production of an image that is input to an optical imaging system (such as a fingerprint reader).

U.S. Pat. No. 4,340,300 to Ruell, the entire contents of which are incorporated herein by reference, teaches a transparent polymer fingerbed that is elastic to form a topographic relief of a finger pattern, the fingerbed facing a sensor plate having a light source coupled to one edge such that the output beam is directed onto a light sensitive are of an electro-optical sensing array for input to an image processing system.

A large body of later patents exists for devices that capture ridge and valley data digitally using optical imaging systems. A variety of other collection techniques have been developed and patented as well that rely on physical properties such as capacitance, infra-red radiation, and ultrasound.

U.S. Pat. No. 5,764,347 to Podmaniczky et al., the entire contents of which are incorporated herein by reference, teaches an optical imaging system between an object plane of a total reflection prism and an image plane, mainly for a fingerprint reading apparatus, comprising an optics for imaging the object plane to the image plane, and an electronic image detector in the image plane. The prism has a first surface receiving light for illuminating the object plane through the interior of the prism and a further surface through which light reflected from the object plane passes towards the optics.

U.S. Pat. No. 6,069,969 to Keagy et al., the entire contents of which are incorporated herein by reference, teaches a thin, inexpensive, removable platen for a direct fingerprint reader without a permanently attached platen, wherein the platen is removable and is formed as a transparent area on a credit card, passport or identification card or as a separate card. The portable platen on the card is inserted over an imaging area of a direct fingerprint reader and light from the direct fingerprint reader passes through an optical surface formed on the underside of the portable platen, is reflected off the fingerprint and passes back through the optical surface to the imaging apparatus where the image is digitized and analyzed and having the optical surface is formed such that the incident light is not refracted away from the fingerprint and the reflected light from the fingerprint is not refracted away from the imaging apparatus.

U.S. Pat. No. 6,150,665 to Suga, the entire contents of which are incorporated herein by reference, teaches a fingerprint detecting device including a flat transparent body, a light source, a thin surface film layer, a fluid layer, and an image detection unit, wherein the transparent body on which a skin surface of a finger is pressed has a surface constituted by a scattering surface with a fine three-dimensional unevenness such that the light source irradiates incident light from inside of the transparent body on the skin surface pressed against the surface of the transparent body, the surface film layer is formed on the surface of the transparent body via a small gap, on which a three-dimensional pattern of the skin surface is transferred by pressing the finger, the fluid layer is formed by sealing one of a gas and a liquid in the gap between the surface of the transparent body and the surface film layer, and is pressed by the surface film layer on which the three-dimensional pattern of the skin surface is transferred and the image detection unit detects an image fingerprint pattern on the basis of the light from the light source, the reflection of which is changed at the surface of the transparent body, when the surface film layer comes into contact with the surface of the transparent body in accordance with the three-dimensional pattern of the skin surface.

U.S. Pat. No. 6,185,319 to Fujiwara, the entire contents of which are incorporated herein by reference, teaches a fingerprint input apparatus that includes a prism, a light source, a pinhole, and an imaging plane, wherein the prism is placed such that a surface in one direction serves as a fingerprint collection surface, the light source irradiates light on the fingerprint collection surface through the prism, the pinhole is set in the path of light which is reflected by the pattern surface of a finger placed on the fingerprint collection surface and emerges from the prism such that the light emerging from the prism and passing through the pinhole is formed into an image on the imaging plane and when the prism is substituted by air, an optical fingerprint collection surface equivalent to the fingerprint collection surface is set to be substantially parallel to the imaging plane.

None of these systems capture forensic quality ridge and valley signatures and DNA samples. However, there are existing optical imaging systems, known as LiveScan systems, which capture forensic quality ridge and valley signatures directly into a digitized format as opposed to traditional ink and paper methods. There are also various means of collecting DNA samples. For instance, existing methods include blood drawing, hair pulling, and buccal swabbing.

Livescan refers to the use of a computer-based device which reads the fingerprint patterns of a subject directly from the subject's fingers. Therefore, the prints are collected into an electronic medium from a "live" person's fingers rather than being read from an inked paper card.

The device typically uses a specially coated glass platform or platen upon which the subject's fingers are rolled or pressed. Images are captured from underneath the platen by one or multiple Charged Couple Device cameras (CCD) or one or multiple CMOS cameras and converted into digital files. Captured images, along with the demographic information about the subject, can then be transmitted electronically to a central database for print comparison.

For example, LiveScan systems are available from sources listed in TABLE 1.

TABLE 1

| Name | Web Address |
|---|---|
| Cross Match Technologies | http://www.crossmatch.com |
| Heimann Biometric Systems | http://www.hbs-jena.com/ |
| Identix | http://www.identix.com/ |
| Printrak | http://www.printrakinternational.com/ |

Cross Match Technologies manufactures a LiveScan device on which a silicone film is placed directly on a platen and the person presses directly into the silicone film to enhance fingerprint image quality. The film is not removable on a person-by-person basis and is not designed to collect DNA.

While LiveScan is designed to capture both rolled and slapped fingerprints, other devices that capture one or several fingerprints not conforming to the FBI specification exist. Single digit capture devices which capture one digit at a time are available from sources listed in TABLE 2.

TABLE 2

| Name | Web Address |
| --- | --- |
| Cross Match Technologies | http://www.crossmatch.com |
| Exact ID | http://www.exactid.com/ |
| Identix | http://www.identix.com/ |
| Secugen | http://www.secugen.com |

These systems may not collect forensic quality images as defined above by the FBI and none of these existing single digit capture devices also collects DNA.

Another significant problem of most prior art optical imaging systems is that these may produce ridge and valley signatures that are distorted due to movement of the ridge and valley area on the surface of the scanning device as the ridge and valley area is being scanned. Observed distortions include smudging and stretching of ridge and valley patterns. All prior art systems do not possess the capability to optionally acquire DNA samples as the ridge and valley signatures are being collected.

Regardless of the collection method, each prior art forensic quality ridge and valley signature results in data presumed to uniquely identify an individual to those skilled in the art of fingerprint identification. Usage of the ridge and valley signatures in this way makes ridge and valley signature association with an individual a very valuable biometric tool.

Most of the prior art DNA sampling techniques are unsuitable for mass collection of DNA samples. For example, invasive prior art techniques, such as finger pricking, blood drawing, and oral swab, can easily create situations in which the system monitor and the subject are both placed at risk. In addition, the system monitor must have special training. A less invasive technique, such as skin scraping, is also not acceptable since preparation to take the sample may irritate the subject due to removal of body hair or live skin tissue. In each of these cases, maintaining the training and the tools required for DNA sampling can be very costly.

A prior art technique to take DNA samples from a subject's ridge and valley areas provides a non-invasive method in which preparation is minimal and the risks to all parties are minimized. U.S. Pat. No. 6,355,439 to Chung, et al., the entire contents of which are incorporated herein by reference, teaches a method and a combined kit for taking a sample of the epidermis by means of an adhesive sheet and storing the sample, and extracting DNA from the epidermis sample stuck to the adhesive sheet.

Published U.S. Patent Application No. 20020037094, by Salva Calcagno and Eduardo Luis, the entire contents of which are incorporated herein by reference, discloses a safety identification device for collecting fingerprints and DNA related material from an individual, for use in verifying the identity of an individual, such as in documents and forms. The device comprises at least one layer for collecting and retaining the fingerprint and the material from the individual, and at least another layer attached to the at least one layer for protecting and preserving the material for determining the DNA of the individual. This patent application considers the use of OCR for fingerprint matching. OCR, or Optical Character Recognition, is used extensively for reading alphabetic characters but, as those skilled in the art know, OCR is not used for matching fingerprints. Further, this patent application teaches collection from only the fingers of an individual and does not consider collection from the remainder of the hands or the feet. Salva Calcagno and Eduardo Luis do not teach or suggest collection of forensic quality ridge and valley signatures. For example, as a subject applies their ridge and valley signatures to a DNA capture film, certain portions of the ridges may not contribute to the DNA sample since there is no bio-matter on that portion of the skin. Hence, when the DNA capture labels are enhanced there are breaks in the ridge patterns. Likewise, there may be filled-in portions in the valleys as some portions of the valleys may contain excessive bio-matter. For these reasons, the ridge and valley signatures obtained with the method of Calcagno et al. cannot meet the stringent requirements of being classified as forensic quality ridge and valley signatures. Calcagno et al. teaches an invention that is noninvasive and uses DNA capture film to acquire a sample of a subject's DNA. However, its non-invasive DNA collection system fails to provide for the collection of forensic quality ridge and valley signatures, at the same time or otherwise.

WO 97/18009, the entire contents of which are incorporated herein by reference, discloses a system and a kit for non-invasive collection of DNA-bearing material from the inner cheeks of a living person or corpse. This includes swabs of high modulus fibers that scrape DNA material from the inner cheeks to obtain sufficient material for future identification. It specifically teaches away from sampling cells from skin. It also mentions a kit that includes the swabs and a means for obtaining and recording ink fingerprints.

U.S. Pat. No. 6,168,922 to Harvey, et al., incorporated herein by reference, discloses devices and methods for the collection, storage, and purification of nucleic acids, such as DNA or RNA, from fluid samples for subsequent genetic characterization, primarily by conventional amplification methods. It can be used to collect, store, or purify nucleic acids either from a biological source other than untreated whole blood, the biological source having naturally occurring nucleic acid amplification inhibitors present, (including either a buccal swab, cerebrospinal fluid, feces, lymphatic fluid, a plasma sample, a saliva sample, a serum sample, urine, or a suspension of cells or viruses), or from a treated whole blood source that has naturally occurring nucleic acid amplification inhibitors present, as well as added blood stabilization components that also inhibit nucleic acid amplification. In particular, an absorbent material that does not bind nucleic acids irreversibly is impregnated with a chaotropic salt. A biological source sample is contacted with the impregnated absorbent material. Any nucleic acids present in the biological source can be either eluted or resolubilized off the absorbent material.

Therefore, in view of the above-described references, there still exists a need for a noninvasive DNA collection system that captures forensic quality DNA samples and ridge and valley signatures (forensic quality or otherwise), during a single data collection window, to increase the available DNA database collection as well as improve the efficiency, effectiveness, safety, quality, and cost-effectiveness of DNA and fingerprint sample collection. That there has been a long-felt need for such a forensic quality system is indicated by the length of time that has elapsed since the filing of the first patent cited above that teaches capturing live fingerprints, some 29 years, without the invention of such a system.

SUMMARY OF THE INVENTION

A system that collects DNA samples and ridge and valley signatures from the same subject during the same collection window adds value to forensic data collection processes. Since collection of the DNA samples and ridge and valley signatures occur during the same collection window, it can be assured that the DNA sample and ridge and valley signature identify the same individual. As the body of DNA samples grows in such a fashion, more crimes may be efficiently solved because many more DNA samples exist with which to accurately identify alleged criminals.

The apparatus and method of the present invention provide a system and method for noninvasive forensic DNA sampling and forensic quality ridge and valley signature collection, comprising:

at least one DNA capture film (typically a rigid DNA capture sheet or plate or a flexible DNA capture film) that captures DNA samples non-invasively;

for a single subject during a single collection window, means for collecting both a DNA sample using this DNA capture film and for collecting at least one forensic quality ridge and valley signature;

means for specifying an identifier for linking the collected DNA sample and the collected ridge and valley signature(s);

in one preferred embodiment, an optical system as the means for capturing forensic quality ridge and valley signatures;

means for improving the capture of ridge and valley signatures by using the principle of adhesion to reduce smudges and distortions.

In a typical embodiment, samples are collected using a transparent DNA capture film having opposed first and second surfaces typically with a substrate sandwiched between the surfaces. The first surface has an adhesive to remove biological matter such as dead skin and oils from the ridge and valley surface using the principle of adhesion. If the system uses total internal reflectance to optically capture ridge and valley signature images, the second surface may provide a film such as a silicone film or an adhesive silicone film so that air bubbles between the film and the platen will be completely removed. Air bubbles in this type of system will image the bubbles very well thereby corrupting the ridge and valley signature images.

Thus, a free standing DNA capture film comprising opposed first and second surfaces may be employed, the first surface comprising adhesive and the second surface comprising a material having a surface energy sufficient to adhere to a platen made of glass or transparent solid polymer (for example acrylates or polycarbonates having few, if any defects, or other materials suitable for platens), such that presence of bubbles between the film and the platen is sufficiently avoided to capture forensic quality fingerprints. By free standing film is meant a film before being used, e.g., placed on a platen.

The system for capturing ridge and valley signatures may employ energy waves, such as light as described above, or other energy waves such as electromagnetic waves, capacitance, infra-red or sonic, e.g., ultrasound based systems. When the term imaging system is used in the context of capturing ridge and valley signatures, this term is taken to mean any system that captures a digital or analog representation of ridge and valley signatures.

For use with optical systems the capture film is typically transparent. Other systems such as direct optical systems that do not rely on total internal reflectance, as well as capacitance, infra-red and sonic, e.g., ultrasound based systems or other energy wave based systems, could use either such a silicone film or any other adhesive film that does not corrupt the quality of the images, e.g., an sonic based system may employ transparent or opaque films. The substrates upon which the adhesive film is placed can be any of a variety of polymer substrates, typically polymer films. Examples of suitable polymer films include polyester, polycarbonate and nylon, for example. Silicone sheets or films are also suitable substrates for the DNA capture film. The substrates may be flexible or rigid and are generally insoluble in water or other materials they may contact.

In a preferred embodiment, a forensic quality ridge and valley signature is captured optically using a high-resolution image sensor such as a digital camera in conjunction with optics.

If desired the invention employs a process for a system monitor to collect a sample according to a preferred embodiment, which comprises soliciting and recording demographic data as well as combined collection of ridge and valley signature data and DNA. In an alternative embodiment DNA samples and the ridge and valley signatures are captured during the same collection window but not simultaneously, i.e., different subprocesses are employed for each type of sample.

BRIEF DESCRIPTION OF THE DRAWINGS

FIG. 1b illustrates a side view of the prior art optical scanning system of FIG. 1a.

FIG. 2b illustrates one or more implementations of a side view of the DNA capture film of FIG. 2a.

FIG. 2c illustrates one or more implementations of a side view of the DNA Capture film of FIG. 2a.

FIG. 3b illustrates a side view of the DNA capture film of FIG. 3a.

DETAILED DESCRIPTION OF THE PREFERRED EMBODIMENTS

Figure 1A:
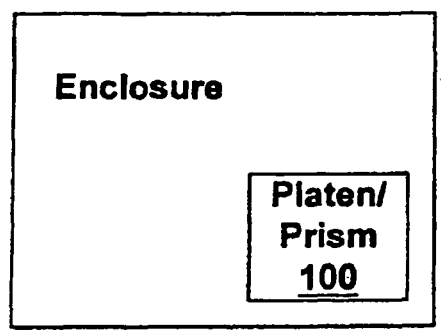
FIG. 1a illustrates a top view of a prior art optical scanning system for the capture of ridge and valley signatures.
Figure 1B:
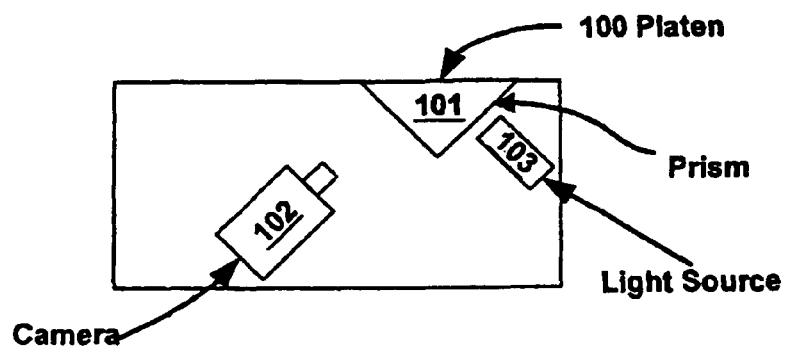

FIGS. 1a and 1b illustrate a top view of an optical scanning system for the capture of ridge and valley signatures for use in the present invention. In the embodiment shown in FIGS. 1a and 1b, a forensic quality ridge and valley signature is captured optically using a high-resolution image sensor such as a digital camera 102 in conjunction with optics. The optics commonly used comprise right angle prisms 101 that apply the principle of total internal reflection to create a ridge and valley image. The top 100 of the right angle prism 101 on which a ridge and valley containing area is placed for signature capture is called the optical platen 100.

Figure 2A:
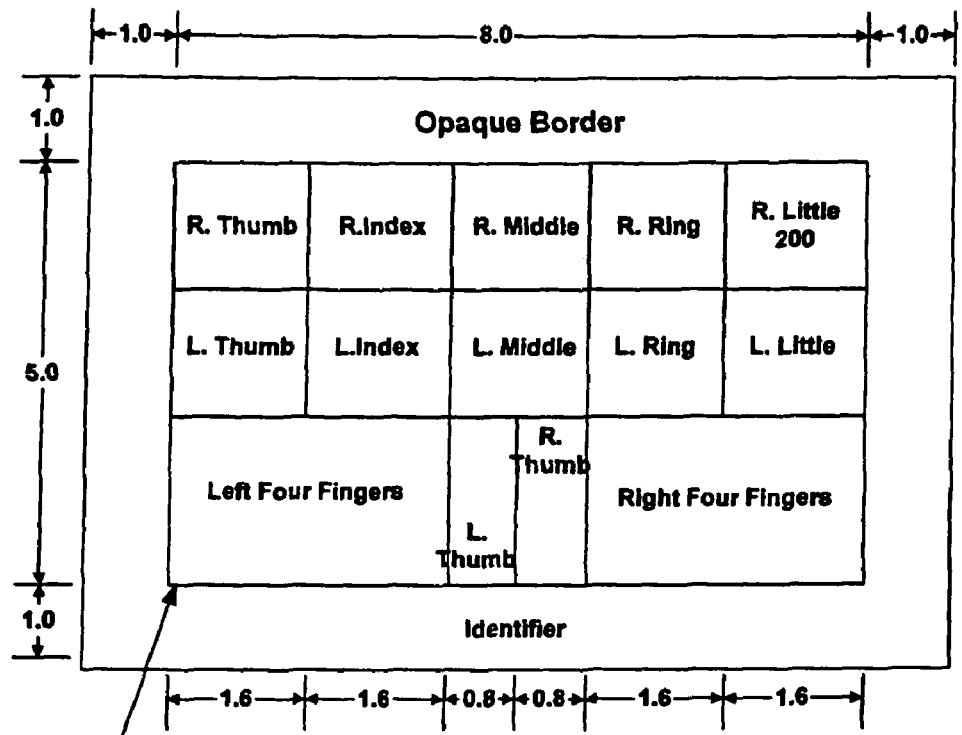
FIG. 2a illustrates a top view of one type of DNA capture film for use with an optical scanning system according to the present invention for simultaneous DNA and ridge and valley signature collection.
Figure 3A:
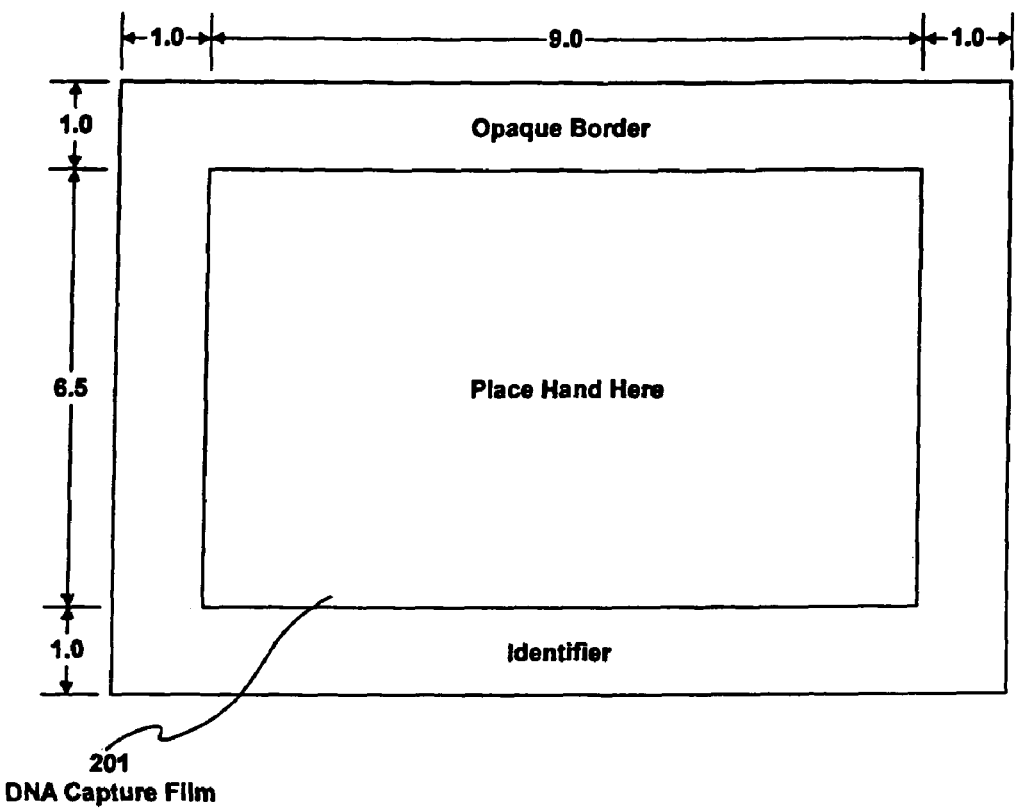
FIG. 3a illustrates a top view of a DNA capture film for use in non-optical DNA sampling.
Figure 6:
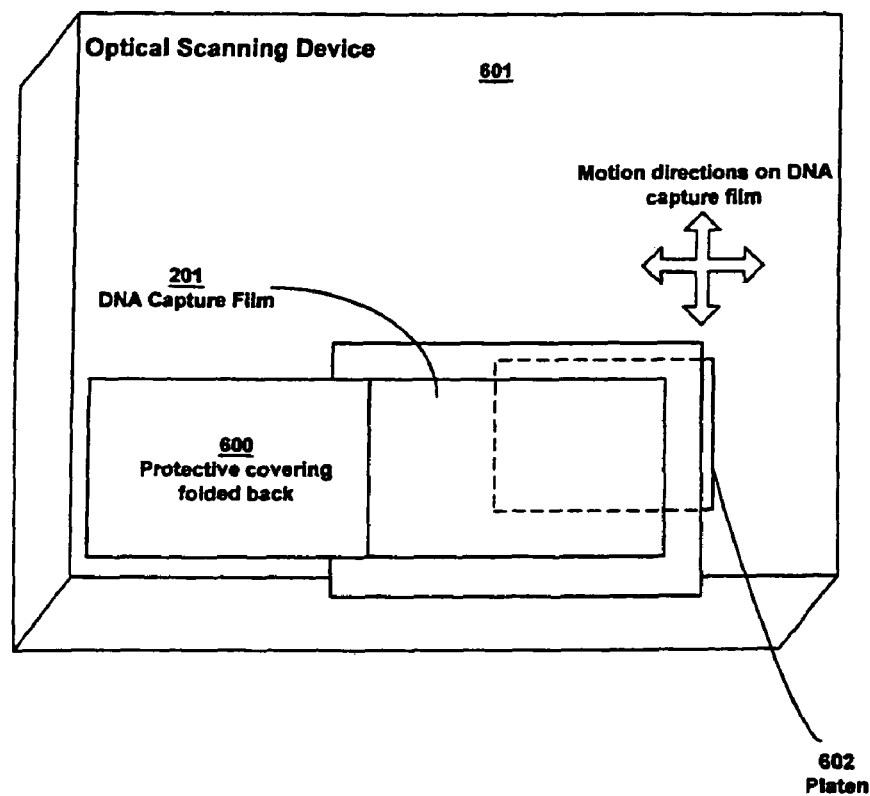
FIG. 6 illustrates an embodiment of a system comprising a DNA capture film and an optical scanning system for the simultaneous capture of DNA samples and ridge and valley signatures, according to the present invention.

FIG. 6 shows a typical embodiment of an optical scanning system, for the capture of ridge and valley signatures for use in the present invention, wherein DNA samples are collected using a transparent DNA capture film 201. FIGS. 2a and 3a show a top view of the capture film 201 wherein relative dimensions are listed for typical embodiments in inches.

Typical DNA capture films are selected from adhesive sheet, as taught by Chung, et al., U.S. Pat. No. 6,355,439, or other suitable DNA capture films.

Figure 2B:
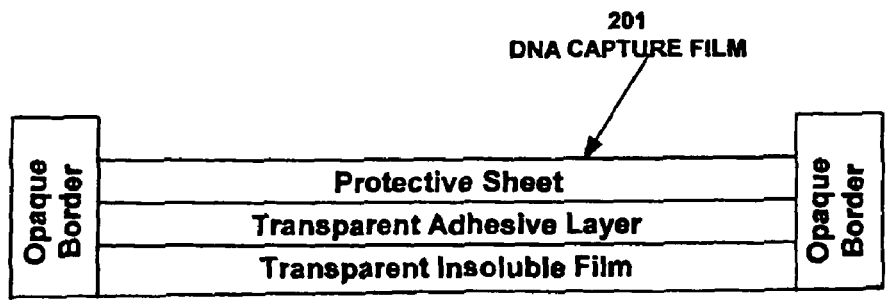
Figure 2C:
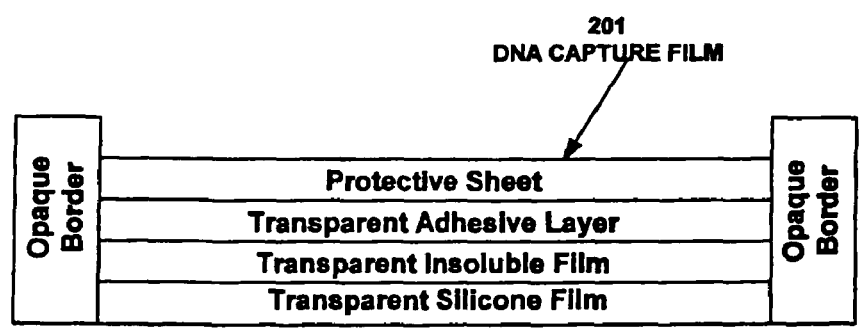

FIG. 2b shows an embodiment of the capture film 201 having opposed first and second surfaces typically with a substrate (transparent insoluble film) sandwiched between the surfaces (see FIG. 2b). The first surface has a transparent adhesive layer to remove biological matter such as dead skin and oils from the ridge and valley surface using the principle of adhesion. In FIG. 2b the substrate itself provides the second surface. Typically there is also a protective sheet above the adhesive (See FIG. 2b). The capture sheet of FIG. 2b may be employed with a system using total internal reflectance to optically capture ridge and valley signatures. However, if desired, a modified capture film 201 may be employed, with the system using total internal reflectance to optically capture ridge and valley signature images, wherein the second surface may provide a film such as a silicone film (FIG. 2c) so that air bubbles between the film 201 and the platen 602 (see FIG. 6) will be completely removed. Air bubbles in this type of system are undesirable because the system will image the bubbles very well thereby corrupting the ridge and valley signature images.

Figure 4:
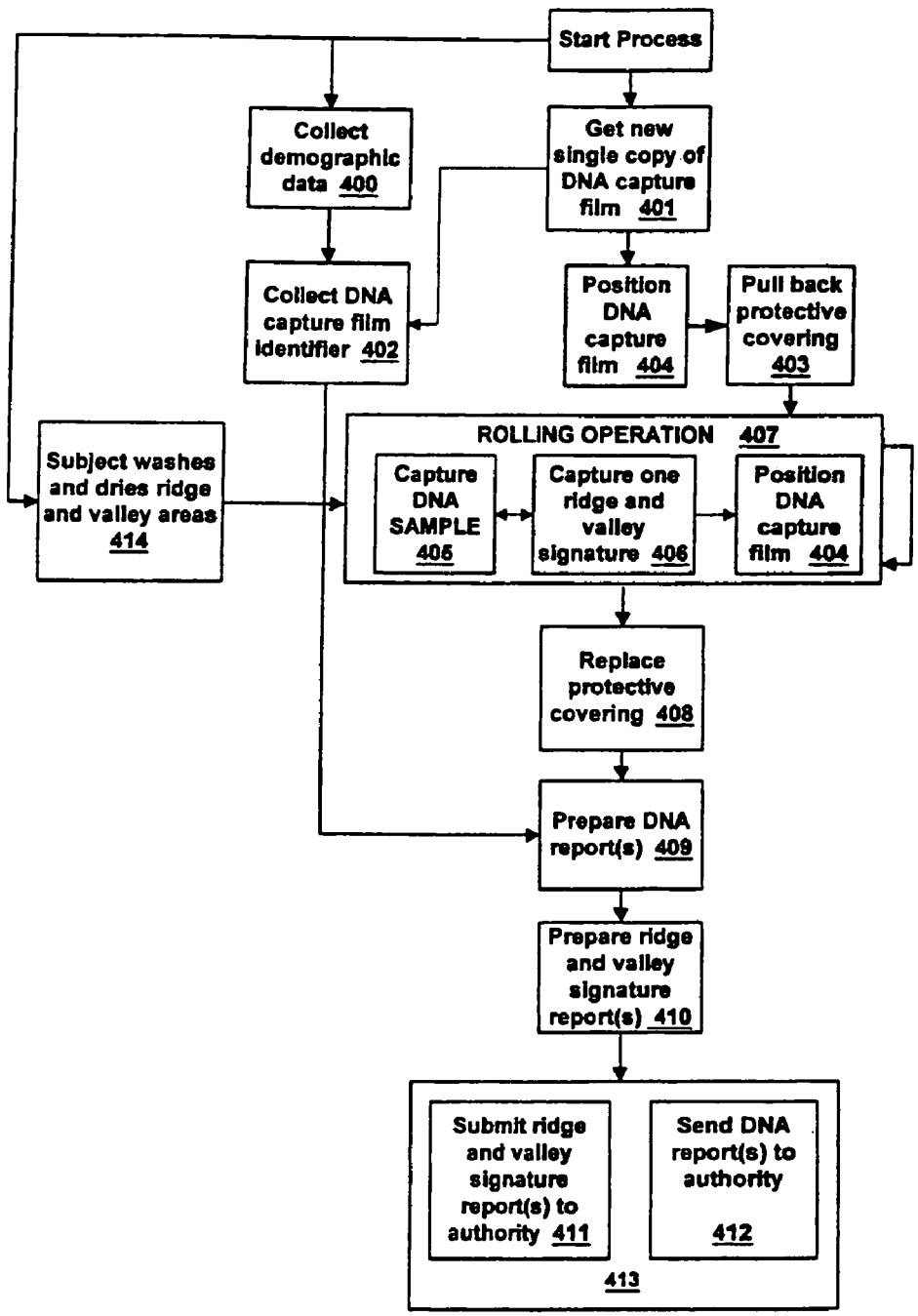
FIG. 4 illustrates a process flow diagram of simultaneous capture of DNA samples and ridge and valley signatures during the same collection window and using the same capture medium, according to the present invention.

FIG. 4 illustrates a preferred embodiment of a process wherein a system monitor (person operating the system) uses an embodiment of the present invention, for example the embodiment of FIG. 6, to collect a sample. The process comprises soliciting and recording demographic data 400 as well as combined collection of ridge and valley signature data and DNA. In the process illustrated in FIG. 4, the system monitor prepares a transparent DNA capture film by first obtaining a new transparent DNA capture film 401. After obtaining the new, DNA capture film 401, the DNA capture film identifier as imprinted, manually or otherwise, on the DNA capture film border is collected 402. Typical ways to provide an identifier include but are not limited to preprinted bar codes, dynamically generated bar codes, computer generated identifiers, and computer reference numbers, such as an existing case number or other personal identification number such as a social security number or even the test subject's name.

The DNA capture film is positioned and secured on top of the scanning device's platen 404, typically with spring clips, and the protective covering of the DNA capture film is pulled back 403. Next, combined capture of a DNA sample and a ridge and valley signature is accomplished 405, 406. The system monitor continually repositions and secures the DNA capture film so that the next area from which a sample is to be taken is placed completely over the platen 404. By moving the film, total internal reflection based systems will not have degraded images from biological material left on the film. Note that systems not based on total internal reflectance may not require that the film be moved since the biological material may not interfere with capturing high quality images. As the subject has a DNA sample taken from each of the areas to be captured, an optical image of the ridge and valley structure is taken simultaneously. A benefit of using the adhesive DNA capture film is that as the ridge and valley signatures are collected in a rolled manner, i.e., by rolling a ridge and valley area over the capture film, distortions and smudges will be reduced in the resulting images since the adhesive inhibits the subject from moving the ridge and valley area that is on top of the platen. Upon completion of DNA and ridge and valley sample collection, the system monitor replaces the protective covering on the DNA capture film 408, removes the DNA capture film from the platen, prepares the necessary report(s) that incorporate the appropriate demographic data and DNA capture film identifier 409, 410, sends DNA capture film and associated report(s) to the appropriate DNA extraction laboratory 412, and sends the ridge and valley signature report(s) to the appropriate governing authorities 411.

Figure 5:
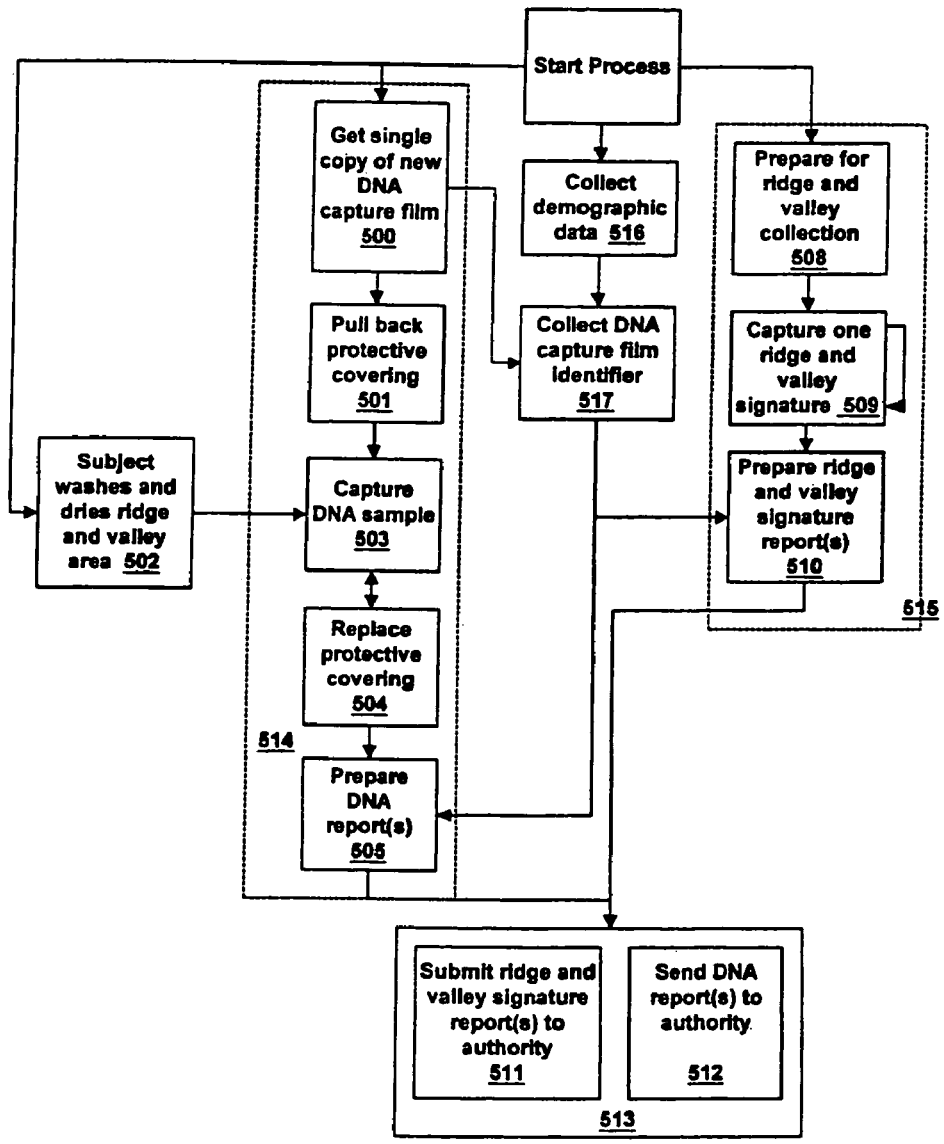
FIG. 5 illustrates the process flow for combined capturing of DNA samples and ridge and valley signatures using separate capture media non-simultaneously during the same collection window, according to the present invention.

FIG. 5 shows an alternative embodiment wherein DNA samples and the ridge and valley signatures are captured during the same collection window but not simultaneously, i.e., different subprocesses are employed for each type of sample. In FIG. 5, a DNA sample is collected using a DNA capture film 500, e.g., adhesive film, and ridge and valley signatures are separately captured 509 using a capture vehicle, e.g., ink impressions applied to a paper fingerprint card or even using optical imaging. The reports generated 505, 510 utilize the collected demographic data 516 and the DNA capture film identifier as applied, manually or otherwise, to the DNA capture film, i.e., the demographic data and DNA capture film identifier are associative, linking the DNA sample and ridge and valley signatures together as originating with a single subject.

The collection process starts when a subject arrives to have ridge and valley signatures and/or DNA samples taken. Referring to FIGS. 4 and 5 if a DNA sample is being collected, the subject is asked to wash and dry their hands or feet 414, 502. It is important that the hands and/or the feet be clean to ensure that the DNA sample will reflect the subject's DNA and not that of someone or something that the subject recently came in contact with. However, it is also acceptable to sample DNA from an individual without having recently washed their hands. In such cases, stricter controls can be adopted and/or outcomes can be handled effectively as long as it is known a mixed sample could be obtained. Likewise, the skin should be as dry as possible so that if an adhesive label is being used to collect DNA this label can collect a substantial enough sampling of bio-matter from the skin of the subject. The system monitor continuously observes the forensic DNA sampling guidelines as outlined above when a DNA sample is to be taken.

Regardless of what type(s) of sample are being collected, the system monitor asks questions of the subject so that demographic data and other data is collected 400, 516. Demographic data may include the subject's name, address, phone number, social security number, and other identifying data to be used to associate the collected samples with the subject for future identification and for entry into databases for future reference.

The process for the capture of DNA varies according to the system monitor's local policy. In the preferred embodiment illustrated in FIG. 4, optical capture of the ridge and valley signatures and DNA samples capture occur simultaneously while in another preferred embodiment illustrated in FIG. 5 the ridge and valley signatures and DNA samples use different capture technologies for each data type. Both FIGS. 4 and 5 illustrate capture from a single subject during a single collection window.

When DNA sampling is to take place, the system monitor removes a single copy of a new DNA capture film 401, 500 from a sanitary container.

At a point after the DNA capture film has been removed from the sanitary container, the DNA capture film identifier is collected 402, 517. In a preferred embodiment, a computer program can generate this DNA capture film identifier and the identifier is then applied to the border of the DNA capture film. In another preferred embodiment, the DNA capture film itself may be pre-printed with this identifier so that collection of the identifier is merely reading the identifier on the DNA capture film border, manually or otherwise, for inclusion with the demographic data.

In the preferred embodiment illustrated in FIG. 4, the system monitor then places the DNA capture film 201 onto the optical imaging system to position 404 the portion of the DNA capture film marked "R. Little" 200 (FIG. 2*a*; for Right Little finger) above the platen 602. The system monitor ensures any spring clips, intended to maintain the position of the DNA capture film on the optical scanning device 601, are properly positioned. At the same time, the system monitor ensures the spring clips never contact the DNA capture film throughout the capture process. Should the spring clips touch the DNA capture film, this DNA capture film is considered to be contaminated and must be discarded and a new DNA capture film together with a new label must be obtained and used to ensure the DNA capture film and label are not contaminated. Referring now to FIGS. 2*a*, 4, 5, and 6, the system monitor pulls back 403, 501 the protective covering of the film 600.

Referring now to FIG. 4, illustrating combined and simultaneous sample capture, once the DNA capture film has been secured above the platen 602, e.g., with spring clips, and the protective covering has been pulled back 403 the system monitor picks up the subject's Right Little finger and rolls the fingerprint of the Right Little finger onto the area of the DNA capture film 201 marked as "R. Little" 200. During this rolling operation, a DNA sample of the subject's "R. Little" finger is captured 405 by the DNA capture film 201 at the same time the optical imaging system 601 takes an optical image 406 of the ridges and valleys of the subject's "R. Little" finger. Referring now to FIG. 5 illustrating non-simultaneous collection during the same collection window, either the DNA sample or the ridge and valley signatures are collected during separate subprocesses 514 and 515.

For simultaneous capture, the system monitor moves a fingerprint identification card bearing the capture film, or upon which the capture film is placed, to the next position on the DNA capture film ensuring that the next fingerprint position of the card is completely above the platen 602. When the DNA capture film has been properly placed into the next position, the system monitor either rolls the fingerprint as appropriate or takes a slap print as appropriate. The repositioning of the DNA capture film continues until all required ridge and valley signature areas have been captured. In a preferred embodiment, each DNA capture film has ten positions for rolled fingerprints—one position for each finger and thumb. It also has four positions for slap prints—prints that are taken by merely setting one's fingers on the surface and applying pressure. The slap positions are for the left four fingers together, the right four fingers together, the left thumb and the right thumb. For non-simultaneous capture the ridge and valley signature collection device is manipulated in a similar fashion to obtain a full set of ridge and valley signatures from the subject.

Figure 3B:
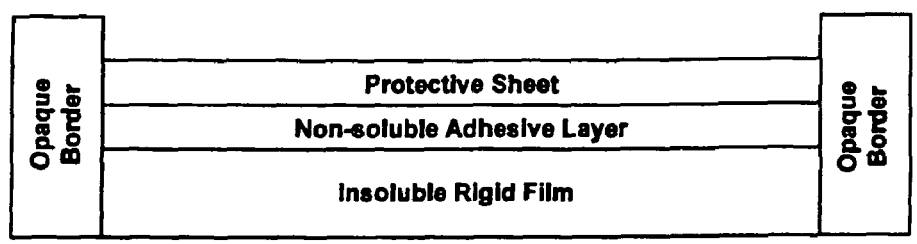

In the non-simultaneous case, a DNA capture film 201, as illustrated in FIGS. 3*a*, 3*b*, may be used for a DNA sample collection. In this case, the system monitor prepares the DNA capture film 500, 501 and then the subject may apply an entire hand or foot to the DNA capture film 201. In all preferred embodiments of the invention, only small amounts of DNA samples are actually required; the discussion to this point has provided for over sampling of DNA in the case that multiple DNA extractions must be performed from the same DNA capture film.

In both of the preferred embodiments illustrated in FIGS. 4 and 5, after the DNA samples and ridge and valley signatures have been captured from all of the subject's ridge and valley areas, the DNA samples and the ridge and valley signatures must be prepared for delivery to the appropriate authorities. The first step in making this preparation is to replace the protective covering on the DNA capture film 408, 504. The DNA capture film is then removed from the optical scanning device, as illustrated in FIG. 4. Zero or more reports are generated for each of the DNA sample and the ridge and valley signature sample 409, 410, 505, 510. These reports include portions of the demographic data collected 400, 516. In addition, the DNA capture film identifier may be used in a report to maintain the proper association between the DNA sample, the ridge and valley signatures, and the subject. Reports may be generated manually, electronically, or using both manual and electronic methods. Once the reports are complete, the reports are delivered to the appropriate authority using the delivery method prescribed by the system monitor's organization.

If desired the DNA capture film can be used as sheets (as described above) or a roll configuration (not shown) wherein the film comes off a roll and after use it may be recovered using a take up reel or cutting off the unrolled portion of the rolled film after use for sending to a laboratory for analysis.

Figure 7:
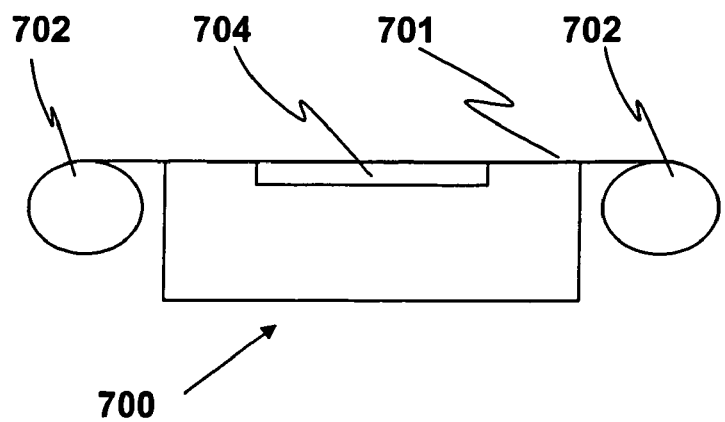
FIG. 7 shows an embodiment of the capture film as a roll between reels.

FIG. 7 shows an embodiment employing the roll configuration which comprises a capture film 701 unreeling on one of reel 702 to be placed over a platen 704 of an imaging device 700 and being taken up after use on another reel 702.

Figure 8:
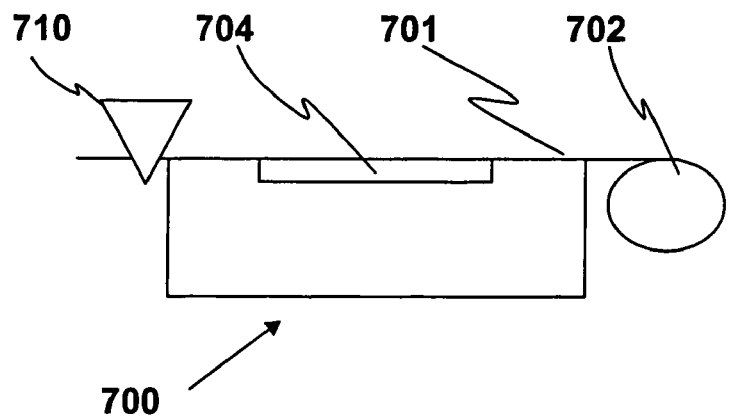
FIG. 8 shows an embodiment employing a capture film unreeling on one reel to be placed over a platen and then cut after use by a knife.

FIG. 8 shows another embodiment employing the roll configuration which comprises a capture film 701 unreeling on one of reel 702 to be placed over a platen 704 of an imaging device 700 and being cut after use by a knife 710. After cutting the cut portion of film is stored.

As one skilled in the art will appreciate, the system and method of the present invention applies to many population groups including, but not limited to, alleged criminals, governmental employees, airport employees, hazardous material drivers, school system employees, sex offenders, unidentified corpses, stock brokerage employees, and public utility employees.

The examples discussed are for illustrative and for discussion purposes only, and are not intended to represent any limiting manner of use of the present invention.

The example of using DNA capture films and optical scanning devices for ridge and valley signature capture is by way of example and is not intended in any limiting sense with respect to use of other noninvasive methods for DNA sample collection or other methods of capturing forensic quality ridge and valley signatures during the same time window. For example, the DNA capture film may be used in ridge and valley signature collection devices whose sensors are based upon the principals of capacitance, infra-red energy, sonic waves, e.g., ultrasound, or other energy waves. Or, capture of fingerprints by a system according to the present invention may not be in accordance with the Live Scan specification (i.e., the system used may capture only a single fingerprint). Further, these systems may not collect forensic quality images, where the FBI has established the definition of forensic quality. Because of this, the DNA film does not have to be optically clear, with clarity depending upon the method of sampling.

In addition, this invention need not be limited to human application. Applications to animals, such as dogs, may be useful for paw prints and DNA samples.

Processing the Sample

The DNA sample may be used in any of a variety of tests. For example, the DNA in the sample can be extracted and analyzed. For example, the cells can be resuspended in a buffer and the DNA extracted using: commercially available kits such as, but not only, DNA IQ and QuickAmp Extraction; proteases such as Proteinase K, detergents such as sodium dodecyl sulfate (SDS) and chaotropic agents such as urea or guanidine and diatomceous earth or silica particles; organic solvent extraction such as phenol/chloroform and DNA precipitation. Some examples of DNA analyses include, but are not limited to, Polymerase Chain Reaction followed by gel electrophoresis; PCR followed by STR fragment analysis; PCR followed by DNA sequencing; Southern Blot analysis; whole genome amplification or replication followed by DNA sequencing or Southern Blot analysis.

In view of the above it is apparent that embodiments other than those described above may come within the spirit and scope of the present invention. Thus, the present invention is not limited by the above-described description but rather is defined by the following claims.

We claim:

1. A method of collecting one or more images of at least one ridge and valley signature and at least one DNA sample from a subject, said method comprising the steps of:
    providing a DNA capture film at a platen of an imaging system configured to collect one or more images of the at least one ridge and valley signature through the platen;
    positioning an area of the subject on the DNA capture film;
    collecting a DNA sample with said DNA capture film; and
    collecting an image, through the DNA capture film, of a ridge and valley signature on the area of the subject positioned on the DNA capture film the subject while the area of the subject is positioned on the DNA capture film.

2. The method of claim 1, further comprising, repositioning the DNA capture film for collecting a second DNA sample and a second image of a ridge and valley signature from another area of the subject.

3. The method of claim 1, further comprising removing the DNA capture film from the platen for processing of the at least one DNA sample collected on the DNA capture film.

4. The method of claim 3, wherein the DNA capture film comprises:
    at least one layer of film that is removably disposed on the platen of the imaging system; and
    a layer of adhesive on a side of the film opposite the platen, wherein the layer of adhesive collects the at least one DNA sample during engagement with the at least one ridge and valley signature of the subject.

5. The method of claim 1, further comprising:
    removing a protective layer from the DNA capture film prior to positioning the area of the subject on the DNA capture film; and
    replacing the protective layer on the DNA capture film subsequent to collection of the image of the ridge and valley signature on the area of the subject.

6. The method of claim 1, further comprising printing an identifier on the DNA capture film that identifies the subject.

7. The method of claim 6, wherein collecting the image, through the DNA capture film, of the ridge and valley signature on the area of the subject positioned on the DNA capture film the subject comprises collecting an image that includes the ridge and valley signature and the identifier.

8. The method of claim 1, further comprising:
    reading the identifier printed on the DNA capture film; and
    correlating the image of the ridge and valley signature with the identifier.

* * * * *